United States Patent
Krüger et al.

(10) Patent No.: US 8,062,995 B2
(45) Date of Patent: Nov. 22, 2011

(54) DIOXAZINE-SUBSTITUTED ARYLAMIDES

(75) Inventors: Bernd-Wieland Krüger, Bergisch Gladbach (DE); Achim Hense, Leverkusen (DE); Bernd Alig, Königswinter (DE); Rüdiger Fischer, Pulheim (DE); Christian Funke, Leichlingen (DE); Ernst Rudolf Gesing, Erkrath (DE); Olga Malsam, Rösrath (DE); Mark Wilhelm Drewes, Langenfeld (DE); Christian Arnold, Langenfeld (DE); Peter Lümmen, Idstein (DE); Erich Sanwald, Kiel (DE)

(73) Assignee: Bayer CropScience AG, Monheim (DE)

( * ) Notice: Subject to any disclaimer, the term of this patent is extended or adjusted under 35 U.S.C. 154(b) by 509 days.

(21) Appl. No.: 11/992,006

(22) PCT Filed: Sep. 5, 2006

(86) PCT No.: PCT/EP2006/008637
§ 371 (c)(1),
(2), (4) Date: Nov. 17, 2008

(87) PCT Pub. No.: WO2007/031213
PCT Pub. Date: Mar. 22, 2007

(65) Prior Publication Data
US 2009/0143228 A1   Jun. 4, 2009

(30) Foreign Application Priority Data
Sep. 15, 2005  (DE) ............... 10 2005 044 108

(51) Int. Cl.
C07D 413/14 (2006.01)
C07D 273/01 (2006.01)
C07C 259/18 (2006.01)
C07C 259/10 (2006.01)
A01N 43/88 (2006.01)

(52) U.S. Cl. .................. 504/223; 544/65
(58) Field of Classification Search ............ 504/223; 544/65
See application file for complete search history.

(56) References Cited

U.S. PATENT DOCUMENTS

| 3,184,500 | A | 5/1965 | Nicolaus et al. |
| 4,404,384 | A | 9/1983 | Gebert et al. |
| 4,987,135 | A | 1/1991 | Haga et al. |
| 6,150,386 | A | 11/2000 | Trah et al. |
| 6,310,005 | B1 * | 10/2001 | Assmann et al. ......... 504/223 |
| 6,699,818 | B1 * | 3/2004 | Walter et al. ......... 504/287 |
| 2003/0229050 | A1 | 12/2003 | Lahm et al. |
| 2004/0138450 | A1 | 7/2004 | Clark |
| 2004/0171114 | A1 | 9/2004 | Gutteridge et al. |
| 2004/0171649 | A1 | 9/2004 | Annis et al. |
| 2004/0186141 | A1 | 9/2004 | Zimmerman |
| 2004/0209923 | A1 | 10/2004 | Berger et al. |
| 2004/0242645 | A1 | 12/2004 | Clark et al. |
| 2005/0124600 | A1 | 6/2005 | Clark et al. |
| 2005/0282868 | A1 | 12/2005 | Finkelstein et al. |
| 2006/0052343 | A1 | 3/2006 | Lahm et al. |

FOREIGN PATENT DOCUMENTS

| CA | 1110642 A | 10/1981 |
| DE | 26 51 083 | 5/1978 |
| DE | 28 20 013 | 11/1979 |
| EP | 0 335 408 A2 | 10/1989 |
| JP | 2003-212834 A | 7/2003 |
| JP | 2005-132727 A | 5/2005 |
| NL | 9202078 | 6/1994 |
| WO | WO 97/00866 A1 | 1/1997 |
| WO | WO 00/15622 A1 | 3/2000 |
| WO | WO 01/49664 A1 | 7/2001 |
| WO | WO 01/70671 A2 | 9/2001 |
| WO | WO 02/094791 A1 | 11/2002 |
| WO | WO 03/015518 A1 | 2/2003 |
| WO | WO 03/015519 A1 | 2/2003 |
| WO | WO 03/016282 A2 | 2/2003 |
| WO | WO 03/016283 A1 | 2/2003 |
| WO | WO 03/016284 A1 | 2/2003 |
| WO | WO 03/016304 A1 | 2/2003 |
| WO | WO 03/024222 A1 | 3/2003 |
| WO | WO 03/027099 A1 | 4/2003 |
| WO | WO 03/062226 A1 | 7/2003 |
| WO | WO 2004/027042 A2 | 4/2004 |
| WO | WO 2004/033468 A1 | 4/2004 |

OTHER PUBLICATIONS

English language abstract for JP 2003-212834, obtained from esp@cenet database on Jul. 11, 2008.
English language abstract for JP 2005-132727, obtained from esp@cenet database on Jul. 11, 2008.
English language abstract for NL 9202078, obtained from esp@cenet database on Jul. 11, 2008.
International Search Report for PCT/EP2006/008637, European Patent Office, The Netherlands, mailed Dec. 12, 2006.

(Continued)

Primary Examiner — Kahsay T Habte
(74) Attorney, Agent, or Firm — Sterne, Kessler, Goldstein & Fox P.L.L.C.

(57) ABSTRACT

Novel dioxazine- and oxdiazine-substituted arylamides of the formula (I)

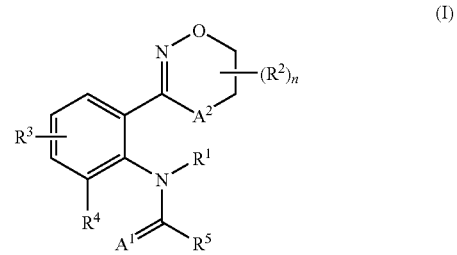

in which $A^1$, $A^2$, $R^1$, $R^2$, $R^3$, $R^4$ and $R^5$ are as defined in the description,
a plurality of processes for preparing these compounds and their use for controlling pests, and also novel intermediates and processes for their preparation.

16 Claims, No Drawings

OTHER PUBLICATIONS

Meyer, E.A. et al., Synthesis and In Vitro Evaluation of 2-Aminoquinazolin-4(3*H*)-one-Based Inhibitors for tRNA-Guanine Transglycosylase (TGT), *Helvetica Chimica Acta 87*:1333-1356, Verlag Helvetica Chimica Acta (2004).

Okada, H. et al., "Synthesis and Antitumor Activities of Prodrugs of Benzoylphenylureas," *Chem. Pharm. Bull. 42*:57-61, Pharmaceutical Society of Japan (1994).

* cited by examiner

DIOXAZINE-SUBSTITUTED ARYLAMIDES

This application is a 35 U.S.C. §371 U.S. National Phase filing of International Application No. PCT/EP2006/008637, filed Sep. 5, 2006, which claims the benefit of German Patent Application No. 10 2005 044 108.4, filed Sep. 15, 2005. Both applications are herein incorporated by reference in their entirety.

The present invention relates to a novel dioxazine- and oxdiazine-substituted arylamides, to a plurality of processes for their preparation and to their use as active compounds, in particular to their use as pesticides.

It is already known that certain substituted 5,6-dihydro-1, 4,2-dioxazines (cf. JP2005132727) have insecticidal and acaricidal properties.

It is also known that certain arylamides (WO 03/016304) and anthranilamides (NL 9202078, WO 01/70671, WO 02/094791, JP 03212,834, WO 03/015519, WO 03/016284, WO 03/015518, WO 03/015519, WO 03/024222, WO 03/016282, WO 03/016283, WO 03/062226, WO 03/027099, WO 2004/027042, WO 2004/033468) have insecticidal properties.

The activity of these compounds is good; however, it is sometimes unsatisfactory.

This invention now provides novel dioxazine- and oxdiazine-substituted arylamides of the formula (I)

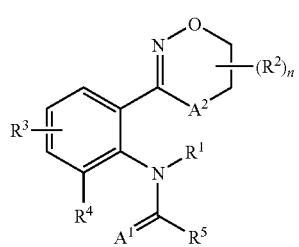

(I)

in which $A^1$ represents oxygen or sulphur, $A^2$ represents oxygen, amino, aminoformyl or aminoacetyl, $R^1$ represents hydrogen, amino, hydroxyl or represents $C_1$-$C_6$-alkyl, $C_2$-$C_6$-alkenyl, $C_2$-$C_6$-alkynyl or $C_3$-$C_6$-cycloalkyl, each of which is optionally mono- or polysubstituted by identical or different substituents, where the substituents independently of one another may be selected from the group consisting of halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino and ($C_1$-$C_4$-alkyl)-$C_3$-$C_6$-cycloalkylamino, $R^2$ independently of one another represent $C_1$-$C_6$-alkyl, $C_2$-$C_6$-alkenyl, $C_2$-$C_6$-alkynyl, $C_3$-$C_6$-cycloalkyl, each of which is optionally mono- or polysubstituted by identical or different substituents, where the substituents independently of one another may be selected from the group consisting of halogen, cyano, nitro, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, ($C_1$-$C_6$-alkoxy)carbonyl, ($C_1$-$C_6$-alkyl)carbonyl and $C_3$-$C_6$-trialkylsilyl, n represents 0 to 4, $R^3$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, $R^4$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^5$ represents a 5- or 6-membered heteroaromatic ring optionally mono- or polysubstituted by identical or different substituents, where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, $C_3$-$C_6$-trialkylsilyl, ($C_1$-$C_4$-alkyl)($C_1$-$C_4$-alkoxy)imino or may furthermore be selected from the group consisting of phenyl, benzoyl, phenoxy, 5- or 6-membered heteroaromatic rings and aromatic 8-, 9- or 10-membered fused heterobicyclic ring systems, where each of the aromatic, heteroaromatic or aromatic heterobicyclic systems may optionally be mono- or polysubstituted by identical or different substituents, where the substituents independently of one another may be selected from the group consisting of $C_1$-$C_6$-alkyl, $C_2$-$C_4$-alkenyl, $C_2$-$C_4$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, ($C_1$-$C_4$-alkyl)amino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_2$-$C_8$-alkyl)aminocarbonyl, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino and $C_3$-$C_6$-trialkylsilyl, where the compounds of the general formula (I) furthermore comprise N-oxides and salts.

Finally, it has been found that the compounds of the formula (I) according to the invention have very good insecticidal properties and can be used both in crop protection and in the protection of materials for controlling unwanted pests, such as insects.

If appropriate, the compounds according to the invention can be present as mixtures of various possible isomeric forms, in particular of stereoisomers, such as, for example, E and Z, threo and erythro, and also optical isomers, and, if appropriate, also of tautomers. What is claimed are both the E and Z isomers, and the threo and erythro, and also the optical isomers, any mixtures of these isomers and also the possible tautomeric forms.

The formula (I) provides a general definition of the arylamides according to the invention. Preferred radical definitions of the formulae mentioned above and below are given below. These definitions apply both to the end products of the formula (I) and, likewise, to all intermediates.

$A^1$ preferably represents oxygen.

$A^1$ furthermore preferably represents sulphur.

$A^1$ particularly preferably represents oxygen.

$A^2$ preferably represents oxygen.

$A^2$ furthermore preferably represents amino.

$R^1$ preferably represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl.

$R^1$ particularly preferably represents hydrogen, methyl, cyclopropyl, cyanomethyl, methoxymethyl, methylthiomethyl, methylsulphinylmethyl or methylsulphonylmethyl.

$R^1$ very particularly preferably represents hydrogen.

$R^2$ independently of one another preferably represent $C_1$-$C_4$-alkyl, $C_3$-$C_6$-cycloalkyl, each of which is optionally mono- or polysubstituted by identical or different substituents, where the substituents independently of one another may be selected from the group consisting of halogen, cyano, nitro, hydroxyl, $C_1$-$C_4$-alkoxy, $C_1$-$C_4$-haloalkoxy, $C_1$-$C_4$-alkylthio, $C_1$-$C_4$-alkylsulphinyl and $C_1$-$C_4$-alkylsulphonyl.

$R^2$ independently of one another particularly preferably represent $C_1$-$C_4$-alkyl, which is in each case optionally mono- or polysubstituted by identical or different substituents, where the substituents independently of one another may be selected from the group consisting of halogen, cyano, nitro, $C_1$-$C_4$-alkoxy, $C_1$-$C_4$-haloalkoxy.

$R^2$ very particularly preferably represents $C_1$-$C_4$-alkyl.

n preferably represents 0 or 1.

n particularly preferably represents 0.

$R^3$ preferably represents hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio.

$R^3$ particularly preferably represents hydrogen, $C_1$-$C_4$-alkyl, $C_1$-$C_2$-haloalkyl, halogen, cyano or $C_1$-$C_2$-haloalkoxy.

$R^3$ very particularly preferably represents hydrogen, methyl, trifluoromethyl, cyano, fluorine, chlorine, bromine, iodine or trifluoromethoxy.

$R^3$ especially preferably represents hydrogen, chlorine, bromine or iodine.

$R^3$ furthermore especially preferably represents cyano.

$R^4$ preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl.

$R^4$ particularly preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl.

$R^4$ very particularly preferably represents methyl, fluorine, chlorine, bromine or iodine.

$R^4$ especially preferably represents methyl or chlorine.

$R^5$ preferably represents a 5-membered heterocyclic ring $R^5$-1 or $R^5$-2,

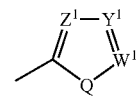

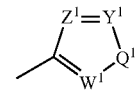

$R^5$ particularly preferably represents a pyrazole or pyrrole ring of the group $R^5$-3 to $R^5$-8, where each $R^5$ is substituted by $R^6$ and may optionally be substituted by $R^7$ or $R^8$ or both $R^7$ and $R^8$.

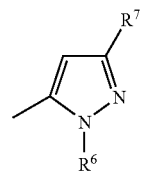

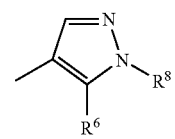

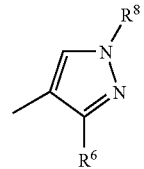

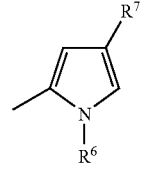

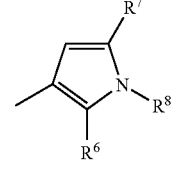

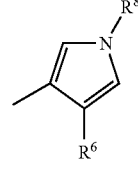

$R^5$ very particularly preferably represents a pyrazole ring $R^5$-3.

$R^6$ preferably represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl or

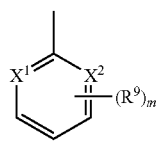

where m=0 to 3, preferably 0 or 1, particularly preferably 0.
$R^6$ particularly preferably represents

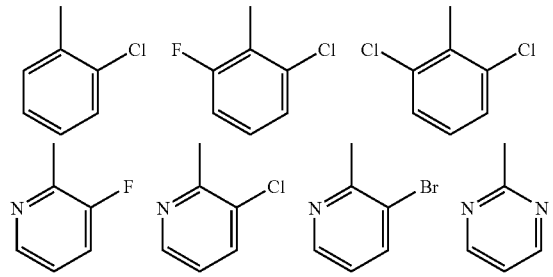

$R^6$ very particularly preferably represents

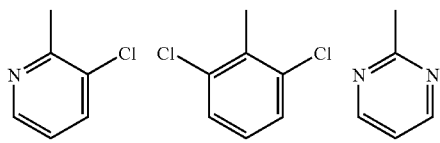

$R^7$ preferably represents hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalkylsulphonyl or ($C_1$-$C_4$-alkyl)$C_1$-$C_4$-alkoxyimino.

$R^7$ particularly preferably represents hydrogen, halogen or $C_1$-$C_4$-haloalkyl.

$R^7$ very particularly preferably represents trifluoromethyl, chlorine or bromine.

$R^8$ preferably represents hydrogen, $C_1$-$C_6$-alkyl or $C_1$-$C_6$-haloalkyl.

$R^8$ particularly preferably represents hydrogen, $C_1$-$C_4$-alkyl or $C_1$-$C_4$-haloalkyl.

$R^9$ preferably represents hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio.

$R^9$ particularly preferably represents hydrogen, $C_1$-$C_6$-haloalkyl or halogen.

$R^9$ very particularly preferably represents hydrogen, $C_1$-$C_2$-haloalkyl, chlorine or bromine.

$Q^1$ represents O, S, N, $NR^6$, $NR^7$ or $NR^8$.

$W^1$, $Y^1$, $Z^1$ independently of one another represent N, $CR^6$, $CR^7$ or $CR^8$.

$X^1$ represents N, CH, CF, CCl, CBr or CI.

$X^1$ preferably represents N or CCl.

$X^2$ represents N or $CR^9$.

$X^2$ preferably represents N or C—$C_1$-$C_6$-haloalkyl or CCl, CBr, CI, CF.

$X^2$ particularly preferably represents N or CCl.

Emphasis is given to compounds of the formula (I-1)

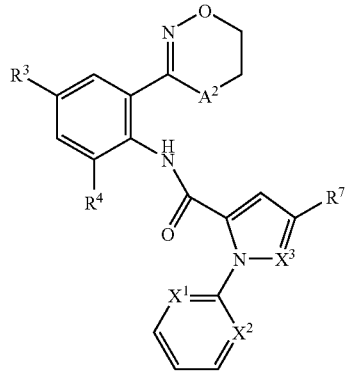

(I-1)

in which $A^2$, $X^1$, $X^2$, $X^3$, $R^3$, $R^4$ and $R^7$ have the stated general, preferred, particularly preferred, very particularly preferred or especially preferred meanings.

$X^3$ is N or CH.

Halogen-substituted radicals, for example haloalkyl, are mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Preferred, particularly preferred or very particularly preferred are compounds which in each case carry the substituents mentioned as being preferred, particularly preferred or very particularly preferred.

Saturated or unsaturated hydrocarbon radicals, such as alkyl or alkenyl, can in each case be straight-chain or branched as far as this is possible, including in connection with heteroatoms, such as, for example, in alkoxy.

Optionally substituted radicals may be mono- or polysubstituted, where in the case of polysubstitution the substituents may be identical or different.

However, the general or preferred radical definitions or illustrations given above can also be combined with one another as desired, i.e. between the respective ranges and preferred ranges. The definitions apply to the end products and also, correspondingly, to precursors and intermediates.

Furthermore, it has been found that dioxazine- and oxdiazine-substituted arylamides of the formula (I) are obtained by one of the processes below.

Dioxazine- and oxdiazine-substituted arylamides of the formula (I-a)

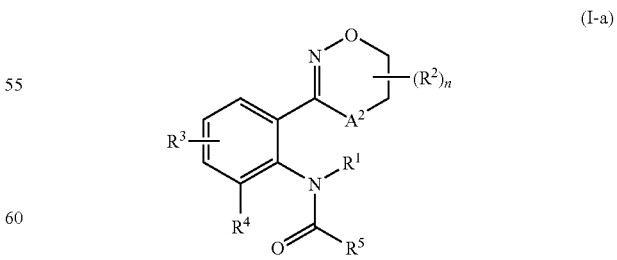

(I-a)

in which $A^2$, $R^1$, $R^2$, $R^3$, $R^4$ and $R^5$ are as defined above are obtained when (A) dioxazine- and oxdiazine-substituted anilines of the formula (II)

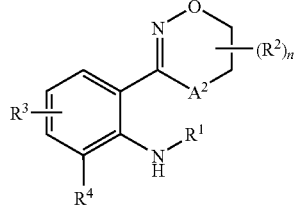

(II)

in which A², R¹, R², R³ and R⁴ are as defined above are reacted with carbonyl chlorides of the formula (III)

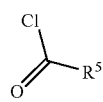

(III)

in which R⁵ is as defined above,
in the presence of an acid binder.

Dioxazine- and oxdiazine-substituted arylthioamides of the formula (I-b)

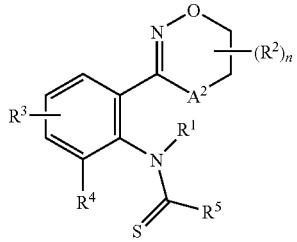

(I-b)

in which A², R¹, R², R³, R⁴ and R⁵ are as defined above are obtained when (B) dioxazine- and oxdiazine-substituted arylamides of the formula (I-a)

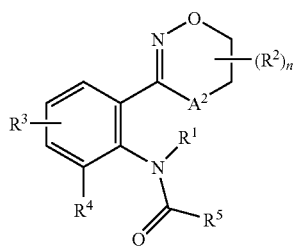

(I-a)

in which A², R¹, R², R³, R⁴ and R⁵ are as defined above, are reacted with a sulphurizing agent.

Illustration of the Processes and Intermediates

Process (A)

Using, for example, 2,4-dichloro-6-(5,6-dihydro-[1,4,2]dioxazin-3-yl)phenylamine and 3-trifluoromethyl-1-(3-chloropyridin-2-yl)-1H-pyrazole-5-carbonyl chloride as starting materials, the course of the process (A) according to the invention can be illustrated by the formula scheme below.

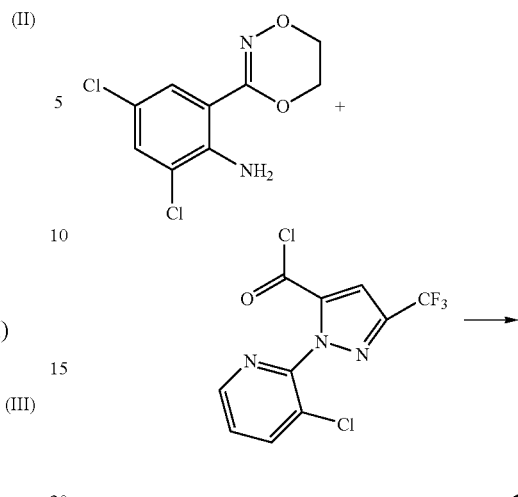

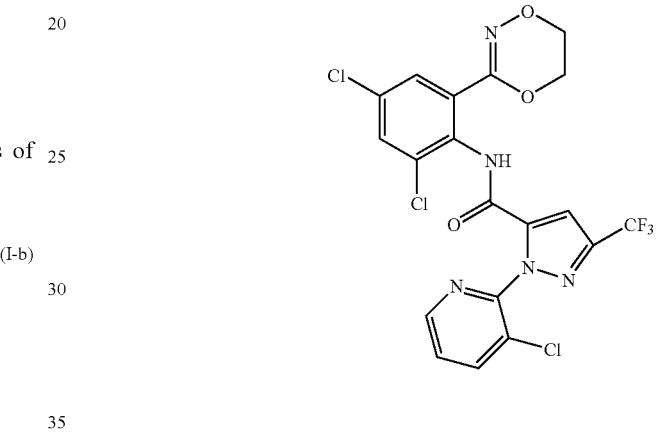

The formula (II) provides a general definition of the dioxazine- and oxdiazine-substituted anilines required as starting materials for carrying out the process (A) according to the invention. In this formula (II), A², R¹, R², R³ and R⁴ preferably, particularly preferably, very particularly preferably and especially preferably have those meanings which have already been mentioned in connection with the description of the compounds of the formula (I) according to the invention as being preferred, particularly preferred, etc., respectively, for these radicals.

The process (A) according to the invention is carried out in the presence of an acid binder. Suitable acid binders are all inorganic or organic bases customary for such coupling reactions. Preference is given to using alkaline earth metal or alkali metal hydrides, hydroxides, amides, alkoxides, acetates, carbonates or bicarbonates, such as, for example, sodium hydride, sodium amide, lithiumdiisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU). It is also possible to use optionally polymer-supported acid binders, such as, for example, polymer-supported diisopropylamine and polymer-supported dimethylaminopyridine.

If appropriate, the process (A) according to the invention can be carried out in the presence of an inert organic diluent, customary for such reactions. These are, for example, aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water. Particular preference is given to using toluene, tetrahydrofuran and N,N-dimethylformamide.

When carrying out the process (A) according to the invention, the reaction temperatures can be varied within a relatively wide range. In general, the process is carried out at temperatures of from 0° C. to 150° C., preferably at temperatures of from 20° C. to 100° C.

Dioxazine- and oxdiazine-substituted anilines of the formula (II) are novel. For $R^1 \neq H$, they can be prepared, for example, by (C) reacting dioxazine-substituted anilines of the formula (II-a) or oxdiazine-substituted anilines of the formula (II-b),

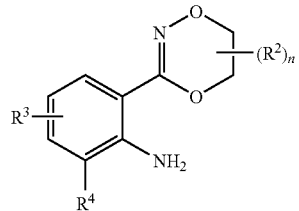

(II-a)

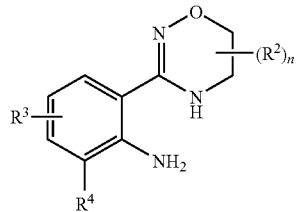

(II-b)

in which $R^2$, $R^3$ and $R^4$ are as defined above, with an alkylating agent (for example $R^1$ halide) in the presence of a base (for example potassium carbonate) in the presence of a diluent (for example tetrahydrofuran or N,N-dimethylformamide) or initially in a condensation reaction (for example with an $R^1$-aldehyde) in the presence of a diluent (for example toluene) and then with a reducing agent (for example sodium cyanoborohydride) in the presence of a diluent (for example methanol).

For compounds of the formula (II) where $R^1$=H, process (C) is unnecessary. Here, the compounds of the formula (II-a) or (II-b) are directly used as starting material for process (A).

Dioxazine-substituted anilines of the formula (II-a) can be prepared, for example, by (D) reacting 2-amino-N-(2-hydroxyethoxy)benzamides of the formula (IV)

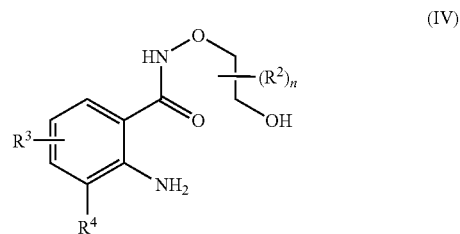

(IV)

in which $R^2$, $R^3$ and $R^4$ are as defined above, with an activating agent (for example thionyl chloride) and, if appropriate, in the presence of a diluent.

When carrying out the process (D) according to the invention, the reaction temperatures can be varied within a relatively wide range. In general, the process is carried out at temperatures of from 0° C. to 150° C., preferably at temperatures of from 60° C. to 80° C.

2-Amino-N-(2-hydroxyethoxy)benzamides of the formula (IV) can be prepared, for example, by (E) reacting 2-aminobenzoic esters of the formula (V),

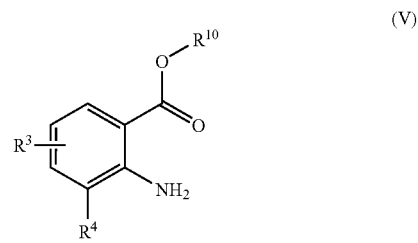

(V)

in which $R^3$ and $R^4$ are as defined above and $R^{10}$ represents $C_1$-$C_4$-alkyl, with 2-aminooxyethanol derivatives of the formula (VI)

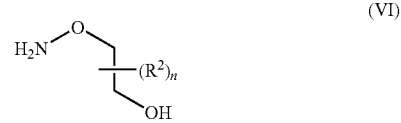

(VI)

in which $(R^2)_n$ is as defined above in the presence of a base (for example sodium methoxide or sodium ethoxide) and also, if appropriate, in the presence of a diluent (for example methanol or ethanol).

2-Aminobenzoic esters of the formula (V) are known or can be obtained by known processes (cf., for example, B. E. A. Meyer, M. Furler, F. Diederich, R. Brenk, G. Klebe, *Helv. Chim. Acta* 2004, 87, 1333-1356).

2-Aminooxyethanol derivatives of the formula (VI) are known or can be obtained by known processes (cf., for example U.S. Pat. No. 3,184,500, DE 2651083, DE 2820013).

Carbonyl chlorides of the formula (III) are known (cf., for example, WO 03/016284, WO 03/016304).

Oxdiazine-substituted anilines of the general formula (II-b) can be prepared, for example, by
(F) reacting oxdiazine-substituted 2-nitrophenyl derivatives of the formula (VII)

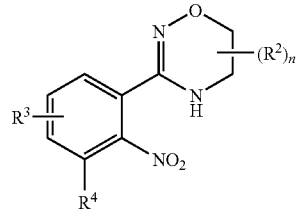

(VII)

in which $R^2$, $R^3$ and $R^4$ are as defined above, with a reducing agent (for example palladium-on-carbon in the presence of hydrogen) in the presence of a diluent (for example ethanol).

Oxdiazine-substituted anilines of the formula (II-b) in which $R^3$ represents 4-chloro, 4-bromo or 4-iodo and $R^2$ and $R^4$ are as defined above can be prepared in an advantageous manner by
(G) reacting oxdiazine-substituted anilines of the general formula (II-b')

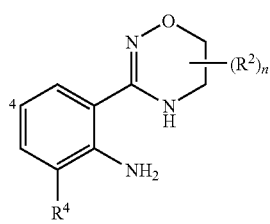

(II-b')

in which $R^2$, $R^4$ and n are as defined above, with a halogenating agent (for example N-chlorosuccinimide, N-bromosuccinimide or N-iodosuccinimide) in the presence of a diluent (for example N,N-dimethylformamide).

When carrying out the process (G) according to the invention, the reaction temperatures can be varied within a relatively wide range. In general, the process is carried out at temperatures of from 0° C. to 150° C., preferably at temperatures of from 80° C. to 120° C.

Oxdiazine-substituted 2-nitrophenyl derivatives of the formula (VII) can be prepared, for example, by
(H) reacting N-alkoxy-2-nitrobenzamidine derivatives of the formula (VIII)

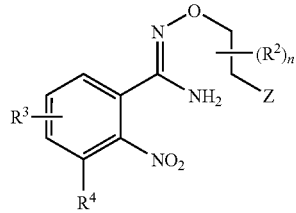

(VIII)

in which $R^2$, $R^3$ and $R^4$ are as defined above and Z represents chlorine, bromine, iodine, methylsulphonyl or tolylsulphonyl, with a base (for example sodium hydride) in the presence of a solvent (for example tetrahydrofuran, dimethylacetamide or N-methylpyrrolidinone).

When carrying out the process (H) according to the invention, the reaction temperatures can be varied within a relatively wide range. In general, the process is carried out at temperatures of from 0° C. to 150° C., preferably at temperatures of from 60° C. to 100° C.

N-Alkoxy-2-nitrobenzamidine derivatives of the formula (VIII) can be prepared, for example, by
(I) reacting N-(2-hydroxyethoxy)-2-nitrobenzamidine derivatives of the formula (IX)

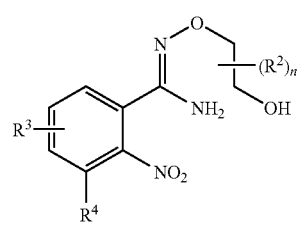

(IX)

in which $R^2$, $R^3$ and $R^4$ are as defined above, with a sulphonyl chloride (for example methylsulphonyl chloride or toluenesulphonyl chloride) or a halogenating agent (for example thionyl chloride), if appropriate in the presence of a solvent (for example dichloromethane) and if appropriate in the presence of a base (for example triethylamine).

When carrying out the process (I) according to the invention, the reaction temperatures can be varied within a relatively wide range. In general, the process is carried out at temperatures of from 0° C. to 150° C., preferably at temperatures of from 0° C. to 60° C.

N-(2-Hydroxyethoxy)-2-nitrobenzamidine derivatives of the formula (IX) can be prepared, for example, by
(J) reacting 2-nitrobenzimino esters of the formula (X)

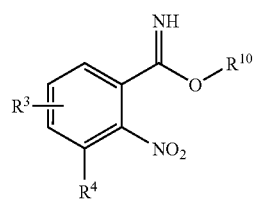

(X)

in which $R^3$ and $R^4$ are as defined above and $R^{10}$ represents $C_1$-$C_4$-alkyl, with 2-aminooxyethanol derivatives of the formula (VI)

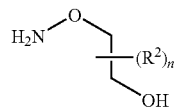

(VI)

in which $R^2$ and n are as defined above in the presence of an inorganic salt (for example ammonium chloride) and in the presence of a diluent (for example methanol or ethanol).

When carrying out the process (J) according to the invention, the reaction temperatures can be varied within a relatively wide range. In general, the process is carried out at temperatures of from 0° C. to 150° C., preferably at temperatures of from 20° C. to 60° C.

2-Nitrobenzimino esters of the formula (X) are known or can be obtained by known processes (cf., for example H. Okada, T. Koyanagi, N. Yamada, *Chem. Pharm. Bull.* 1994, 42, 57-61; EP 335408).

Process (B)

Using, for example, N-[2,4-dichloro-6-(5,6-dihydro-[1,4,2]dioxazin-3-yl)phenyl]-5-bromo-2-(3-chloropyridin-2-yl)-2H-pyrazole-3-carboxamide as starting material and Lawesson's reagent as sulphurizing agent, the course of the process (B) according to the invention can be illustrated by the formula scheme below.

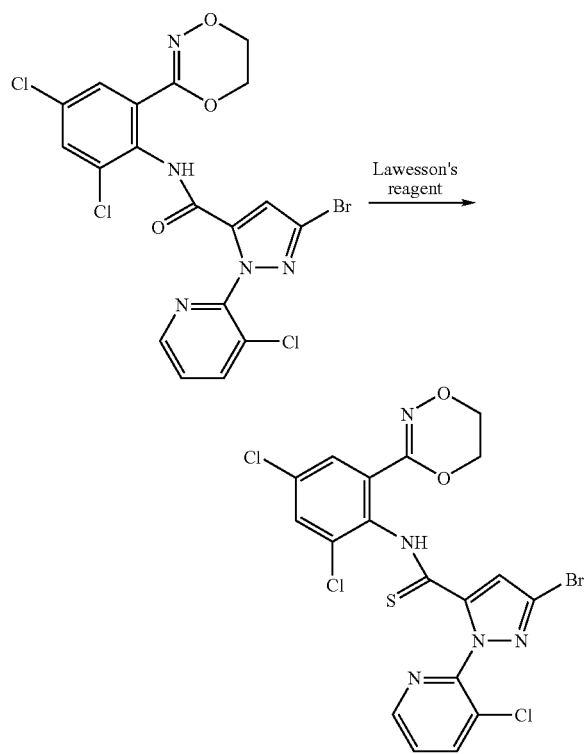

The formula (I-a) provides a general definition of the arylamides required starting materials for carrying out the process (B) according to the invention. In the formula (I-a), $A^2$, $R^1$, $R^2$, $R^3$, $R^4$ and $R^5$ preferably, particularly preferably, very particularly preferably and especially preferably have those meanings which have already been mentioned in connection with the description of the compounds of the formula (I) according to the invention as being preferred, particularly preferred, etc., respectively, for these radicals.

The arylamides of the formula (I-a) are a sub-group of the arylamides of the formula (I) and can be obtained by process (A).

Suitable for the use as sulphurizing agents are all reagents customary for such reactions. Preference is given to using phosphorus pentasulphide and Lawesson's reagent.

The compounds of the formula (I) can, if appropriate, be present in different polymorphic forms or as a mixture of different polymorphic forms. Both the pure polymorphs and the polymorph mixtures are provided by the invention and can be used according to the invention.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control Protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus,* Miridae, *Nezara* spp., *Oebalus* spp., Pentomidae, *Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera,* Cercopidae, *Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotisl* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The compounds of the formula (D) according to the invention have in particular excellent activity against aphids (for example *Myzus persicae*), butterfly caterpillars (for example *Plutella xylostella, Spodoptera frugiperda, Spodoptera exigua, Heliothis armigera*) and beetle larva (for example *Phaedon cochleariae*).

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (*Rickettsia*-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:

Inhibitors of Nucleic Acid Synthesis
: benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid Inhibitors of Mitosis and Cell Division
: benomyl, carbendazim, diethofencarb, ethaboxam, fuberidazole, pencycuron, thiabendazole, thiophanat-methyl, zoxamide Inhibitors of Respiratory Chain Complex I
: diflumetorim Inhibitors of Respiratory Chain Complex II
: boscalid, carboxin, fenfuram, flutolanil, furametpyr, firmecyclox, mepronil, oxycarboxin, penthiopyrad, thifluzamide Inhibitors of Respiratory Chain Complex III
: azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin Decouplers
: dinocap, fluazinam Inhibitors of ATP Production
: fentin acetate, fentin chloride, fentin hydroxide, silthiofam Inhibitors of Amino Acid Biosynthesis and Protein Biosynthesis
: andoprim, blasticidin-S, cyprodinil, kasugamycin, kasugamycin hydrochloride hydrate, mepanipyrim, pyrimethanil Inhibitors of Signal Transduction
: fenpiclonil, fludioxonil, quinoxyfen Inhibitors of Lipid and Membrane Synthesis
: chlozolinate, iprodione, procymidone, vinclozolin
  ampropylfos, potassium-ampropylfos, edifenphos, etridiazole, iprobenfos (IBP), isoprothiolane, pyrazophos
  tolclofos-methyl, biphenyl
  iodocarb, propamocarb, propamocarb hydrochloride, propamocarb-fosetylate Inhibitors of Ergosterol Biosynthesis
: fenhexamid,
  azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidole, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforine, triticonazole, uniconazole, voriconazole, viniconazole, aldimorph, dodemorph, dodemorph acetate, fenpropidin, fenpropimorph, spiroxamine, tridemorph,
  naftifine, pyributicarb, terbinafine Inhibitors of Cell Wall Synthesis
: benthiavalicarb, bialaphos, dimethomorph, flumorph, iprovalicarb, mandipropamid, polyoxins, polyoxorim, validamycin A Inhibitors of Melanin Biosynthesis
: capropamid, diclocymet, fenoxanil, phthalid, pyroquilon, tricyclazole Resistance Inductors
: acibenzolar-S-methyl, probenazole, tiadinil Multisite
: captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Further Fungicides
: amibromdol, benthiazole, bethoxazin, capsimycin, carvone, quinomethionate, chloropicrin, cufraneb, cyflufenamid, cymoxanil, dazomet, debacarb, diclomezine, dichlorophen, dicloran, difenzoquat, difenzoquat metilsulphate, diphenylamine, ferimzone, flumetover, flusulphamide, fluopicolide, fluoroimide, fosetyl-aluminium, fosetyl-calcium, fosetyl-sodium, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyribencarb, pyrrolnitrin, quintozene, tecloftalam, tecnazene, triazoxide, trichlamide, valiphenal, zarilamid,
  2-(2-{[6-(3-chloro-2-methylphenoxy)-5-fluoropyrimidin-4-yl]oxy}phenyl)-2-(methoxyimino)-N-methylacetamide,
  2-[[[[1-[3-(1-fluoro-2-phenylethyl)oxy]phenyl]ethylidene]amino]oxy]methyl]-alpha(methoxyimino)-N-methyl-alpha-benzacetamide,
  cis-1-(4-chlorophenyl)-2-(1H-1,2,4-triazol-1-yl)cycloheptanol,
  1-[(4-methoxyphenoxy)methyl]-2,2-dimethylpropyl-1H-imidazole-1-carboxylic acid,
  2,3,5,6-tetrachloro-4-(methylsulphonyl)pyridine,
  2-butoxy-6-iodo-3-propylbenzopyranon-4-one,
  2-chloro-N-(2,3-dihydro-1,1,3-trimethyl-1H-inden-4-yl)-3-pyridinecarboxamide,
  3,4,5-trichloro-2,6-pyridinedicarbonitrile,
  3,4-dichloro-N-(2-cyanophenyl)isothiazole-5-carboxamide (isotianil)
  3-[5-(4-chlorophenyl)-2,3-dimethylisoxazolidin-3-yl]pyridine,
  5-chloro-6-(2,4,6-trifluorophenyl)-N-[(1R)-1,2,2-trimethylpropyl][1,2,4]triazolo[1,5-a]pyrimidine-7-amine,
  5-chloro-7-(4-methylpiperidin-1-yl)-6-(2,4,6-trifluorophenyl)[1,2,4]triazolo[1,5-a]pyrimidine,
  5-chloro-N-[(1R)-1,2-dimethylpropyl]-6-(2,4,6-trifluorophenyl) [1,2,4]triazolo[1,5-a]pyrimidine-7-amine,
  methyl 2-[[[cyclopropyl[(4-methoxyphenyl)imino]methyl]thio]methyl]-alpha(methoxymethylene)benzacetate,
  methyl 1-(2,3-dihydro-2,2-dimethyl-1H-inden-1-yl)-1H-imidazole-5-carboxylate,
  N-(3',4'-dichloro-5-fluorobiphenyl-2-yl)-3-(difluoromethyl)-1-methyl-1H-pyrazole-4-carboxamide,
  N-(3-ethyl-3,5,5-trimethylcyclohexyl)-3-formylamino-2-hydroxy benzamide,
  N-(4-chloro-2-nitrophenyl)-N-ethyl-4-methylbenzenesulphonamide,
  N-(4-chlorobenzyl)-3-[3-methoxy-4-(prop-2-yn-1-yloxy)phenyl]propanamide,
  N-[(4-chlorophenyl)(cyano)methyl]-3-[3-methoxy-4-(prop-2-yn-1-yloxy)phenyl]propanamide,
  N-(5-bromo-3-chloropyridin-2-yl)methyl-2,4-dichloronicotinamide, N-[1-(5-bromo-3-chloropyridin-2-yl)ethyl]-2,4-dichloronicotinamide,
(2S)—N-[2-[4-[[3-(4-chlorophenyl)-2-propynyl]oxy]-3-methoxyphenyl]ethyl]-3-methyl-2-[(methylsulphonyl)amino]butanamide,
N-{(Z)-[(cyclopropylmethoxy)imino][6-(difluoromethoxy)-2,3-difluorophenyl]methyl}-2-benzacetamide,
N-{2-[1,1'-bi(cyclopropyl)-2-yl]phenyl}-3-(difluoromethyl)-1-methyl-1H-pyrazole-4-carboxamide,
N-{2-[3-chloro-5-(trifluoromethyl)pyridin-2-yl]ethyl}-2-(trifluoromethyl)benzamide,
N-ethyl-N-methyl-N'-{2-methyl-5-(trifluoromethyl)-4-[3-(trimethylsilyl)propoxy]phenyl}imidoformamide,
O-[1-[(4-methoxyphenoxy)methyl]-2,2-dimethylpropyl] 1H-imidazole-1-carbothioic acid,
2-amino-4-methyl-N-phenyl-5-thiazolecarboxamide,
2,4-dihydro-5-methoxy-2-methyl-4-[[[[1-[3-(trifluoromethyl)phenyl]ethylidene]amino]oxy]methyl]phenyl]-3H-1,2,4-triazol-3-one (CAS No. 185336-79-2),
N-(6-methoxy-3-pyridinyl)cyclopropane carboxamide, Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
  Carbamates,
    for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
  Organophosphates,
    for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
  Pyrethroids,
    for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambdacyhalothrin, metofluthrin, permethrin (cis-, trans-), phenothrin (1R-trans-isomer), prallethrin, profluthrin, protrifenbute, pyresmethrin, resmethrin, RU 15525, silafluofen, taufluvalinate, tefluthrin, terallethrin, tetramethrin (1R isomer), tralomethrin, transfluthrin, ZXI 8901, pyrethrins (pyrethrum)
DDT
Oxadiazines,
  for example indoxacarb
Semicarbazone,
  for example metaflumizon (BAS3201)

Acetylcholine Receptor Agonists/Antagonists
  Chloronicotinyls,
    for example acetamiprid, clothianidin, dinotefuran, imidacloprid, nitenpyram, nithiazine, thiacloprid, thiamethoxam
  Nicotine, bensultap, cartap Acetylcholine Receptor Modulators
  Spinosyns,
    for example spinosad GABA-Controlled Chloride Channel Antagonists
  Organochlorine,
    for example camphechlor, chlordane, endosulphan, gamma-HCH, HCH, heptachlor, lindane, methoxychlor
  Fiprols,
    for example acetoprole, ethiprole, fipronil, pyrafluprole, pyriprole, vaniliprole Chloride Channel Activators
  Mectins,
    for example avermectin, emamectin, emamectin-benzoate, ivermectin, lepomectin, milbemycin Juvenile Hormone Mimetics,
  for example diofenolan, epofenonane, fenoxycarb, hydroprene, kinoprene, methoprene, pyriproxifen, triprene Ecdysone Agonists/Disruptors
  Diacylhydrazines,
    for example chromafenozide, halofenozide, methoxyfenozide, tebufenozide Chitin Biosynthesis Inhibitors
  Benzoylureas,
    for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
  Buprofezin
  Cyromazine Oxidative Phosphorylation Inhibitors, ATP Disruptors
  Diafenthiuron
  Organotin compounds,
    for example azocyclotin, cyhexatin, fenbutatin-oxide Oxidative Phosphorylation Decouplers Acting by Interrupting the H-Proton Gradient
  Pyrroles,
    for example chlorfenapyr
  Dinitrophenols,
    for example binapacyrl, dinobuton, dinocap, DNOC, meptyldinocap Site-I electron transport inhibitors METI's,
  for example fenazaquin, fenpyroximate, pyrimidifen, pyridaben, tebufenpyrad, tolfenpyrad
  Hydramethylnon
  Dicofol
Site-II Electron Transport Inhibitors
  Rotenone
Site-III Electron Transport Inhibitors
  Acequinocyl, fluacrypyrim
Microbial Disruptors of the Insect Gut Membrane
  *Bacillus thuringiensis* strains
Lipid Synthesis Inhibitors
  Tetronic acids,
  for example spirodiclofen, spiromesifen
  Tetramic acids,
  for example spirotetramat, cis-3-(2,5-dimethylphenyl)-4-hydroxy-8-methoxy-1-azaspiro[4.5]dec-3-en-2-one
  Carboxamides,
  for example flonicamid
  Octopaminergic agonists,
  for example amitraz
Inhibitors of Magnesium-Stimulated ATPase,
  Propargite
  Nereistoxin analogues,
  for example thiocyclam hydrogen oxalate, thiosultap-sodium
Ryanodine Receptor Agonists,
  Benzodicarboxamides,
  for example flubendiamide
  Anthranilamides,
  for example Rynaxypyr (3-bromo-N-{4-chloro-2-methyl-6-[(methylamino)carbonyl]-phenyl}-1-(3-chloropyridin-2-yl)-1H-pyrazole-5-carboxamide)
Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.
Active compounds with unknown or unspecific mechanisms of action
  Fumigants,
  for example aluminium phosphide, methyl bromide, sulphuryl fluoride
  Antifeedants,
  for example cryolite, flonicamid, pymetrozine
  Mite growth inhibitors,
  for example clofentezine, etoxazole, hexythiazox
  Amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and worms by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Boligard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., Haematobia spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus*; Hymenopterons, such as *Sirex juvencus, Urocerus gigas, Urocerus gigas taignus, Urocerus augur*; Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combination with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Aviculariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The Preparation Examples and Use Examples below illustrate the invention without limiting it.

PREPARATION EXAMPLES

Example 1

1-(6-chloro-2-pyiridvl)-N-(2,4-dichloro-6-(3-(5,6-dihydro-1,4,2-dioxazinyl)phenyl-3-trifluoromethyl-1H-pyrazole-5-carboxamide (I-1-1)

0.266 g (0.857 mmol) of 6-chloro-2-(3-trifluoromethyl-5-chlorocarbonylpyrazolyl)pyridine in 15 ml of toluene are initially charged under argon. 0.192 g of 3-(3,5-dichloro-2-aminophenyl)-5,6-dihydro-1,4,2-dioxine, 0.047 g of (1,6-diazabicyclo[5.4.0]undec-7-ene(1, 5-5)) and 0.185 g (2.337 mmol) of pyridine are added. After 3 h of stirring under reflux, the reaction mixture is cooled and poured into 200 ml of water, and the mixture is extracted three times with in each case 100 ml of ethyl acetate. The extracts are dried with sodium sulphate and evaporated to dryness using a rotary evaporator.

The residue is purified by chromatography on silica gel (cyclohexane/ethyl acetate=3:1).

Yield 0.26 g (60% of theory)

The following compounds of the formula (I-1) are obtained analogously to the Example (I-1-1) shown above and the general description.

TABLE 1

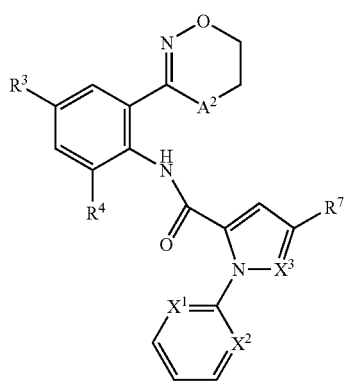

(I-1)

| Ex. No. | $A^2$ | $R^3$ | $R^4$ | $R^7$ | $X^1$ | $X^2$ | $X^3$ | logP |
|---|---|---|---|---|---|---|---|---|
| I-1-2 | O | Cl | Cl | Cl | N | CCl | N | 3.07 |
| I-1-3 | O | H | $CH_3$ | $CF_3$ | N | CCl | N | 3.00 |
| I-1-4 | O | H | $CH_3$ | Br | N | CCl | N | 2.59 |
| I-1-5 | O | Cl | $CH_3$ | Br | N | CCl | N | 3.13 |
| I-1-6 | O | Cl | $CH_3$ | $CF_3$ | N | CCl | N | 3.50 |
| I-1-7 | O | H | $CH_3$ | Cl | N | CCl | N | 2.54 |
| I-1-8 | O | Cl | Cl | Br | N | CCl | N | 3.09 |
| I-1-9 | O | Cl | $CH_3$ | Cl | N | CCl | N | 3.08 |
| I-1-10 | O | Br | $CH_3$ | Cl | N | CCl | N | 3.18 |
| I-1-11 | O | Br | $CH_3$ | $CF_3$ | N | CCl | N | 3.58 |
| I-1-12 | O | Br | $CH_3$ | Br | N | CCl | N | 3.24 |
| I-1-13 | O | Cl | Cl | Br | CCl | CCl | N | 3.98 |
| I-1-14 | O | Cl | $CH_3$ | $CF_3$ | N | N | N | 2.79 |
| I-1-15 | O | Cl | Cl | $CF_3$ | N | N | N | 2.80 |
| I-1-16 | NH | H | $CH_3$ | $CF_3$ | N | CCl | N | 1.98 |
| I-1-17 | NH | H | $CH_3$ | Cl | N | CCl | N | 1.65 |
| I-1-18 | NH | Cl | $CH_3$ | $CF_3$ | N | CCl | N | 2.70 |
| I-1-19 | NH | Cl | $CH_3$ | Br | N | CCl | N | 2.25 |
| I-1-20 | NH | Cl | $CH_3$ | Cl | N | CCl | N | 2.25 |
| I-1-21 | O | Cl | Cl | Br | N | CCl | CH | 3.48 |
| I-1-22 | NH | I | $CH_3$ | Br | N | CCl | CH | 2.39 |
| I-1-23 | NH | I | $CH_3$ | Br | N | CCl | N | 2.21 |
| I-1-24 | NH | I | $CH_3$ | $CF_3$ | N | CCl | N | 2.66 |
| I-1-25 | O | Cl | $CH_3$ | Br | N | CCl | CH | 3.50 |
| I-1-26 | NH | I | $CH_3$ | Cl | N | CCl | N | 2.44 |
| I-1-27 | NH | H | Cl | Br | N | CCl | N | 1.89 |
| I-1-28 | NH | H | $CH_3$ | Br | N | CCl | CH | 1.83 |
| I-1-29 | NH | Br | $CH_3$ | $CF_3$ | N | CCl | N | 2.80 |
| I-1-30 | NH | Br | $CH_3$ | Cl | N | CCl | N | 2.35 |
| I-1-31 | NH | Br | $CH_3$ | Br | N | CCl | N | 2.37 |
| I-1-32 | NH | CN | $CH_3$ | Br | N | CCl | CH | 1.90 |

The logP values given in the tables and Preparation Examples above are determined in accordance with EEC Directive 79/831 Annex V.A8 by HPLC (High Performance Liquid Chromatography) on a reversed-phase column (C 18). Temperature: 43° C.

The determination by LC-MS in the acidic range is carried out at pH 2.7 using 0.1% aqueous formic acid and acetonitrile (contains 0.1% formic acid) as mobile phases; linear gradient from 10% acetonitrile to 95% acetonitrile.

Calibration is carried out using unbranched alkan-2-ones (having 3 to 16 carbon atoms) with known logP values (determination of the logP values by the retention times using linear interpolation between two successive alkanones).

The lambda-max values were determined in the maxima of the chromatographic signals using the UV spectra from 200 nm to 400 nm.

Preparation of Starting Materials of the Formula (II-a)

Example 2

3-(3,5-dichloro-2-aminophenyl)-5,6-dihydro-1,4,2-dioxazine

At 20° C., 30 ml of thionyl chloride are initially charged and 3 g of 3,5-dichloro-2-amino-N-(2-hydroxyethoxy)benzamide are added in 3 portions with stirring. The mixture is stirred at 70° C. for 12 h. The reaction mixture is then cooled and carefully poured onto ice-water. The mixture is extracted twice with in each case 150 ml of dichloromethane and the extracts are dried with sodium sulphate and evaporated to dryness using a rotary evaporator.

Purification by silica gel chromatography cyclohexane/ethyl acetate=10:1.

Yield: 2 g (62% of theory)

Preparation of Starting Materials of the Formula (IV)

Example 3

3,5-dichloro-2-amino-N-(2-hydroxyethoxy)benzamide 9 g (40.9 mmol) of methyl 3,5-dichloro-2-aminobenzoate and 6.3 g (81.8 mmol) of 2-(aminooxy)ethanol are initially charged in 90 ml of methanol, and 22.1 g (122.7 mmol) of sodium methoxide as a 30% strength solution in methanol are added dropwise at 20° C. The mixture is stirred at 50° C. overnight. The mixture is cooled and poured onto 400 ml of water, and the pH is adjusted to 3 using 1 N hydrochloric acid. The mixture is extracted 3 times with in each case 150 ml of ethyl acetate and the extracts are dried with sodium sulphate and concentrated using a rotary evaporator.

Purification by silica gel chromatography cyclohexane/ethyl acetate=3:1, then cyclohexane/ethyl acetate=1:1.

Yield: 4 g (30% of theory)

Preparation of Starting Materials of the Formula (IIb)

Example 4

2-(5,6-dihydro-4H-[1,2,4]oxadiazin-3-yl)-6-methylphenylamine 3 g (13.6 mmol) of 3-(3-methyl-2-nitrophenyl)-5,6-dihydro-4H-[1,2,4]oxadiazine are dissolved in 40 ml of ethanol, and 0.3 g of Pd/C (5%) is added. The mixture is then stirred at 21° C. under a hydrogen pressure of 3 bar for 72 h. The reaction mixture is then filtered and the ethanol is distilled off under reduced pressure.

Yield: 2.5 g

Preparation of Starting Materials of the Formula (VII)

Example 5

3-(3-methyl-2-nitrophenyl)-5,6-dihydro-4H-[1,2,4] oxadiazine 1.4 g (5.4 mmol) of 3-methyl-N-(2-chloroethoxy)-2-nitrobenzamidine are initially charged in 45 ml of 1-methyl-2- pyrrolidone, and 0.18 g (6 mmol) of sodium hydride (80% pure) is added slowly. The mixture is stirred at 100° C. for 12 h, cooled, poured onto water and extracted with ethyl acetate. After drying over sodium sulphate, the solvent is distilled off under reduced pressure.

Yield: 0.75 g

Preparation of Starting Materials of the Formula (VIII)

Example 6

3-methyl-N-(2-chloroethoxy)-2-nitrobenzamidine 4.75 g (19.9 mmol) of 3-methyl-N-(2-hydroxyethoxy)-2-nitrobenzamidine are stirred at 60° C. in 45 ml (617 mmol) of thionyl chloride for 3 h. The mixture is then cooled and carefully poured into water. The mixture is extracted with methylene chloride, the extracts are dried over sodium sulphate and the solvent is distilled off under reduced pressure. The residue is chromatographed on silica gel (cyclohexane: ethyl acetate:=4:1).

Yield: 4.1 g

Preparation of Starting Materials of the Formula (IX)

Example 7

3-methyl-N-(2-hydroxyethoxy)-2-nitrobenzamidine 3.4 g (17.5 mmol) of methyl 3-methyl-2-nitrobenzimine and 2.7 g (35 mmol) of 2-aminooxyethanol are initially charged in 40 ml of ethanol. About 150 mg of ammonium chloride are added and the mixture is stirred at 40° C. for a further 12 h. The mixture is then poured onto 300 ml of water and extracted three times with in each case 100 ml of ethyl acetate, the extracts are dried over sodium sulphate and the organic solvent is then distilled off under reduced pressure.

Yield: 4.3 g (99% of theory)

USE EXAMPLES

Example No. 1

*Myzus persicae* Test
Solvents: 1% of N-methylpyrrolidone (NMP)
  1% of diacetone alcohol
  Dye: brilliant sulphoflavin for staining the water
To produce a suitable preparation of active compound, the active compound is mixed with the stated amounts of solvents and the concentrate is diluted with stained water to the desired concentration.

The *Myzus persicae* are provided with an active compound preparation of the desired concentration for ingestion.

After the desired period of time, the activity in % is determined. 100% means that all aphids have been killed; 0% means that none of the aphids have been killed.

In this test, for example, the following compounds of the Preparation Examples show good activity: I-1-7, I-1-8, I-1-9

TABLE 2

| | *Myzus* test | |
|---|---|---|
| Active compound | Active compound concentration in ppm | Kill rate after 6-7$^d$ in % |
| I-1-7 | 30 | 100 |
| I-1-8 | 30 | 100 |
| I-1-9 | 30 | 100 |

Example No. 2

*Aedes aegypti* Test
Solvents: 1% of N-methylpyrrolidone (NMP)
  1% of diacetone alcohol
  Dye: brilliant sulphoflavin for staining the water
To produce a suitable preparation of active compound, the active compound is mixed with the stated amounts of solvents and the concentrate is diluted with stained water to the desired concentration.

The larvae (*Aedes aegypti*) are treated with an active compound preparation of the desired concentration.

After the desired period of time, the activity in % is determined. 100% means that all of the larvae have been killed; 0% means that none of the larvae have been killed.

In this test, for example, the following compound of the Preparation Examples shows good activity: I-1-8

TABLE 3

| | *Aedes aegypti* test | |
|---|---|---|
| Active compound | Active compound concentration in ppm | Kill rate after 2-4$^d$ in % |
| I-1-8 | 30 | 100 |

Example No. 3

*Diabrotica undecimpunctata* (DIABUN)
Solvents: 1% of N-methylpyrrolidone (NMP)
  1% of diacetone alcohol
  Dye: brilliant sulphoflavin for staining the water
To produce a suitable preparation of active compound, the active compound is mixed with the stated amounts of solvents and the concentrate is diluted with stained water to the desired concentration.

The eggs (*Diabrotica undecimpunctata*) are treated with an active compound preparation of the desired concentration.

After the desired period of time, the activity in % is determined. 100% means that all animals have been killed; 0% means that none of the animals have been killed.

In this test, for example, the following compounds of the Preparation Examples show good activity: I-1-5, I-1-8, I-1-9

TABLE 4

| | *Diabrotica undecimpunctata* test | |
|---|---|---|
| Active compound | Active compound concentration in ppm | Kill rate after 2-5$^d$ in % |
| I-1-5 | 300 | 100 |
| I-1-8 | 300 | 100 |
| I-1-9 | 300 | 100 |

Example No. 4

*Heliothis virescens*
Solvents: 1% of N-methylpyrrolidone (NMP)
  1% of diacetone alcohol
  Dye: brilliant sulphoflavin for staining the water
To produce a suitable preparation of active compound, the active compound is mixed with the stated amounts of solvents and the concentrate is diluted with stained water to the desired concentration.

The eggs (*Heliothis virescens*) are treated with an active compound preparation of the desired concentration.

After the desired period of time, the activity in % is determined. 100% means that all animals have been killed; 0% means that none of the animals have been killed.

In this test, for example, the following compounds of the Preparation Examples show good activity: I-1-7, I-1-8, I-1-9

TABLE 5

*Heliothis virescens* test

| Active compound | Active compound concentration in ppm | Kill rate after 6-7$^d$ in % |
|---|---|---|
| I-1-7 | 300 | 100 |
| I-1-8 | 100 | 100 |
| I-1-9 | 300 | 100 |

Example No. 5

Phaedon Test
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After the desired period of time, the activity in % is determined. 100% means that all beetle larvae have been killed; 0% means that none of the beetle larvae have been killed.

In this test, for example, the following compounds of the Preparation Examples show good activity: I-1-1, I-1-2, I-1-5, I-1-6, I-1-8, I-1-9, I-1-10, I-1-11, I-1-12, I-1-13, I-1-16, I-1-17, I-1-18, I-1-19, I-1-20, I-1-22, I-1-23, I-1-24, I-1-25, I-1-26, I-1-29, I-1-30, I-1-32, I-1-21, I-1-28

TABLE 6

Phaedon test

| Active compound | Active compound concentration in g/ha | Kill rate after 7$^d$ in % |
|---|---|---|
| I-1-1 | 500 | 100 |
| I-1-2 | 100 | 100 |
| I-1-5 | 100 | 83 |
| I-1-6 | 100 | 100 |
| I-1-8 | 100 | 100 |
| I-1-9 | 100 | 100 |
| I-1-10 | 100 | 100 |
| I-1-11 | 100 | 100 |
| I-1-12 | 100 | 100 |
| I-1-13 | 100 | 100 |
| I-1-16 | 100 | 100 |
| I-1-18 | 100 | 100 |
| I-1-19 | 100 | 100 |
| I-1-20 | 100 | 100 |
| I-1-22 | 100 | 100 |
| I-1-23 | 100 | 100 |
| I-1-24 | 100 | 100 |
| I-1-25 | 100 | 83 |
| I-1-26 | 100 | 100 |
| I-1-29 | 100 | 100 |
| I-1-30 | 100 | 100 |
| I-1-32 | 100 | 100 |

TABLE 6-continued

Phaedon test

| Active compound | Active compound concentration in g/ha | Kill rate after 7$^d$ in % |
|---|---|---|
| I-1-28 | 100 | 100 |
| I-1-21 | 100 | 100 |

Example No. 6

Myzus Test (MYZUPE Spray Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier and the concentrate is diluted with emulsifier-containing water to the desired concentration.

Discs of Chinese cabbage (*Brassica pekinensis*), which are infested by all stages of the green peach aphid (*Myzus persicae*) are sprayed with an active compound preparation of the desired concentration.

After the desired period of time, the activity in % is determined. 100% means that all aphids have been killed; 0% means that none of the aphids have been killed.

In this test, for example, the following compounds of the Preparation Examples show good activity: I-1-2, I-1-16, I-1-17, I-1-18, I-1-19, I-1-20, I-1-22, I-1-23, I-1-24, I-1-26, I-1-29, I-1-30

TABLE 7

*Myzus* test (spray treatment)

| Active compound | Active compound concentration in g/ha | Kill rate after 5$^d$ in % |
|---|---|---|
| I-1-2 | 100 | 80 |
| I-1-16 | 100 | 100 |
| I-1-17 | 100 | 100 |
| I-1-18 | 100 | 100 |
| I-1-19 | 100 | 90 |
| I-1-20 | 100 | 100 |
| I-1-22 | 100 | 100 |
| I-1-23 | 100 | 90 |
| I-1-24 | 100 | 90 |
| I-1-26 | 100 | 100 |
| I-1-29 | 100 | 100 |
| I-1-30 | 100 | 100 |

Example No. 7

*Spodoptera frugiperda* Test (SPODFR Spray Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier and the concentrate is diluted with emulsifier-containing water to the desired concentration.

Discs of maize leaves (*Zea mays*) are sprayed with an active compound preparation of the desired concentration and after drying populated with caterpillars of the army worm (*Spodoptera frugiperda*).

After the desired period of time, the activity in % is determined. 100% means that all of the caterpillars have been killed; 0% means that none of the caterpillars have been killed.

In this case, for example, the following compounds of the Preparation Examples show good activity: I-1-1, I-1-2, I-1-3, I-1-4, I-1-5, I-1-6, I-1-7, I-1-8, I-1-9, I-1-10, I-1-11, I-1-12, I-1-16, I-1-17, I-1-18, I-1-19, I-1-20, I-1-22, I-1-23, I-1-24, I-1-25, I-1-26, I-1-29, I-1-30, I-1-32, I-1-21, I-1-28

TABLE 8

Spodoptera test (spray treatment)

| Active compound | Active compound concentration in g/ha | Kill rate after $7^d$ in % |
|---|---|---|
| I-1-1 | 500 | 100 |
| I-1-2 | 100 | 100 |
| I-1-3 | 100 | 100 |
| I-1-4 | 100 | 100 |
| I-1-5 | 100 | 100 |
| I-1-6 | 100 | 100 |
| I-1-7 | 100 | 100 |
| I-1-8 | 100 | 100 |
| I-1-9 | 100 | 100 |
| I-1-10 | 100 | 100 |
| I-1-11 | 100 | 100 |
| I-1-12 | 100 | 100 |
| I-1-16 | 100 | 100 |

| Active compound | Active compound concentration in g/ha | Kill rate after 7d in % |
|---|---|---|
| I-1-17 | 100 | 100 |
| I-1-18 | 100 | 100 |
| I-1-19 | 100 | 100 |
| I-1-20 | 100 | 100 |
| I-1-22 | 100 | 100 |
| I-1-23 | 100 | 100 |
| I-1-24 | 100 | 100 |
| I-1-25 | 100 | 83 |
| I-1-26 | 100 | 100 |
| I-1-29 | 100 | 100 |
| I-1-30 | 100 | 100 |
| I-1-32 | 100 | 100 |
| I-1-28 | 100 | 100 |
| I-1-21 | 100 | 100 |

Example No. 8

*Spodoptera frugiperda* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier and the concentrate is diluted with water to the desired concentration.

Maize plants (*Zea mays*) are watered with an active compound preparation of the desired concentration and infected with *Spodoptera frugiperda* larvae.

After the desired period of time, the kill in % is determined. 100% means that all larvae have been killed; 0% means that none of the larvae have been killed.

In this test, for example, the following compounds of the Preparation Examples show good activity: I-1-1, I-1-3, I-1-6, I-1-8, I-1-9, I-1-10, I-1-11

TABLE 9

Spodoptera test (treatment by watering)

| Active compound | Active compound concentration in ppm | Kill rate after $14^d$ in % |
|---|---|---|
| I-1-1 | 20 | 95 |
| I-1-3 | 20 | 95 |
| I-1-6 | 20 | 98 |
| I-1-8 | 20 | 95 |
| I-1-9 | 20 | 95 |
| I-1-10 | 20 | 90 |
| I-1-11 | 20 | 98 |
| I-1-17 | 20 | 98 |
| I-1-18 | 20 | 95 |
| I-1-19 | 20 | 95 |
| I-1-20 | 20 | 95 |

Example No. 9

*Spodoptera exigua* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier and the concentrate is diluted with emulsifier-containing water to the desired concentration.

Cabbage leaves (*Brassica oleracea*) are treated by being dipped into the active compound preparation of the desired concentration and populated with caterpillars of the army worm (*Spodoptera exigua*) while the leaves are still moist.

After the desired period of time, the kill in % is determined. 100% means that all caterpillars have been killed; 0% means that none of the caterpillars have been killed.

In this test, for example, the following compounds of the Preparation Examples show good activity: I-1-1, I-1-6, I-1-10, I-1-11, I-1-16, I-1-17, I-1-18, I-1-19, I-1-20

TABLE 10

Spodoptera exigua test

| Active compound | Active compound concentration in ppm | Kill rate after $7^d$ in % |
|---|---|---|
| I-I-1 | 20 | 100 |
| I-1-6 | 100 | 100 |
| I-1-10 | 20 | 100 |
| I-1-11 | 20 | 100 |
| I-1-16 | 20 | 100 |
| I-1-17 | 4 | 100 |
| I-1-18 | 100 | 100 |
| I-1-19 | 4 | 80 |
| I-1-20 | 4 | 100 |

Example No. 10

*Heliothis armigera* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier and the concentrate is diluted with emulsifier-containing water to the desired concentration.

Soya bean leaves (*Glycine max.*) are treated by being dipped into the active compound preparation of the desired concentration and populated with caterpillars of the cotton bollworm (*Heliothis armigera*) while the leaves are still moist.

After the desired period of time, the kill in % is determined. 100% means that all caterpillars have been killed; 0% means that none of the caterpillars have been killed.

In this test, for example, the following compounds of the Preparation Examples show good activity: I-1-1, I-1-8, I-1-9, I-1-10, I-1-11, I-1-16, I-1-17, I-1-18, I-1-19, I-1-20

TABLE 11

Heliothis armigera test

| Active compound | Active compound concentration in ppm | Kill rate after $7^d$ in % |
| --- | --- | --- |
| I-1-1 | 20 | 100 |
| I-1-8 | 20 | 100 |
| I-1-9 | 20 | 80 |
| I-1-10 | 20 | 100 |
| I-1-11 | 20 | 100 |
| I-1-16 | 20 | 100 |
| I-1-17 | 4 | 100 |
| I-1-18 | 20 | 100 |
| I-1-19 | 4 | 100 |
| I-1-20 | 4 | 100 |

Example No. 11

*Spodoptera exigua* Test; Resistant Strain
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier and the concentrate is diluted with emulsifier-containing water to the desired concentration.

Cabbage leaves (*Brassica oleracea*) are treated by being dipped into the active compound preparation of the desired concentration and populated with caterpillars of the army worm (*Spodoptera exigua*, resistant strain) while the leaves are still moist.

After the desired period of time, the kill in % is determined. 100% means that all caterpillars have been killed; 0% means that none of the caterpillars have been killed.

In this test, for example, the following compounds of the Preparation Examples show good activity: I-1-1, I-1-6, I-1-10, I-1-11, I-1-17, I-1-18, I-1-19

TABLE 12

Spodoptera exigua test; resistant strain

| Active compound | Active compound concentration in ppm | Kill rate after $7^d$ in % |
| --- | --- | --- |
| I-1-1 | 100 | 100 |
| I-1-6 | 20 | 100 |
| I-1-10 | 20 | 100 |
| I-1-11 | 20 | 80 |
| I-1-17 | 4 | 100 |
| I-1-18 | 100 | 100 |
| I-1-19 | 20 | 100 |

Example No. 12

*Plutella* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier and the concentrate is diluted with emulsifier-containing water to the desired concentration.

Cabbages leaves (*Brassica oleracea*) are treated by being dipped into the active compound preparation of the desired concentration and populated with caterpillars of the diamondback moth (*Plutella xylostella*) while the leaves are still moist.

After the desired period of time, the kill in % is determined. 100% means that all caterpillars have been killed; 0% means that none of the caterpillars have been killed.

In this test, for example, the following compounds of the Preparation Examples show good activity: I-1-1, I-1-6, I-1-11, I-1-16, I-1-17, I-1-18, I-1-19, I-1-20

TABLE 13

Plutella test

| Active compound | Active compound concentration in ppm | Kill rate after $7^d$ in % |
| --- | --- | --- |
| I-1-1 | 100 | 100 |
| I-1-6 | 20 | 100 |
| I-1-11 | 20 | 80 |
| I-1-16 | 100 | 100 |
| I-1-17 | 4 | 100 |
| I-1-18 | 20 | 100 |
| I-1-19 | 0.8 | 100 |
| I-1-20 | 4 | 100 |

Example No. 13

*Myzus persicae* Test; Systemic Treatment
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier and the concentrate is diluted with water to the desired concentration.

The active compound preparation is mixed with water. The stated concentration refers to the amount of active compound per volume unit of water (mg/l=ppm). The treated water is filled into vessels with a pea plant (*Pisum sativum*) which is then infected with the green peach aphid (*Myzus persicae*).

After the desired period of time, the kill in % is determined. 100% means that all aphids have been killed; 0% means that none of the aphids have been killed.

In this test, for example, the following compounds of the Preparation Examples show good activity: I-1-16, I-1-18, I-1-19

TABLE 14

Myzus persicae test; systemic treatment

| Active compound | Active compound concentration in ppm | Kill rate after $6^d$ in % |
| --- | --- | --- |
| I-1-16 | 20 | 100 |
| I-1-18 | 20 | 95 |
| I-1-19 | 20 | 90 |

Example No. 14

*Myzus* Test; Oral
Solvent: 80 parts by weight of acetone

To produce a suitable preparation of active compound, 1 part by weight of active compound is mixed with the stated amounts of solvent and the concentrate is diluted with water to the desired concentration.

Vessels are populated with all stages of the green peach aphid (*Myzus persicae*) which are treated by sucking the active compound preparation of the desired concentration.

After the desired period of time, the activity in % is determined. 100% means that all aphids have been killed; 0% means that none of the aphids have been killed.

In this test, for example, the following compounds of the Preparation Examples show good activity: I-1-1, I-1-16, I-1-22, I-1-23, I-1-24

TABLE 15

*Myzus persicae* test; oral

| Active compound | Active compound concentration in ppm | Kill rate after $5^d$ in % |
|---|---|---|
| I-1-16 | 100 | 100 |
| I-1-22 | 100 | 100 |
| I-1-23 | 100 | 100 |
| I-1-24 | 100 | 100 |

Example No. 15

*Aphis gossypii* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier and the concentrate is diluted with emulsifier-containing water to the desired concentration.

Cotton leaves (*Gossypium hirsutum*) which are heavily infested by the cotton aphid (*Aphis gossypii*) are treated by being dipped into the active compound preparation of the desired concentration.

After the desired period of time, the kill in % is determined. 100% means that all aphids have been killed; 0% means that none of the aphids have been killed.

In this test, for example, the following compounds of the Preparation Examples show good activity: I-1-19, I-1-20

TABLE 16

*Aphis gossypii* test

| Active compound | Active compound concentration in ppm | Kill rate after $6^d$ in % |
|---|---|---|
| I-1-19 | 100 | 80 |
| I-1-20 | 100 | 80 |

The invention claimed is:

1. A compound of formula (I-1):

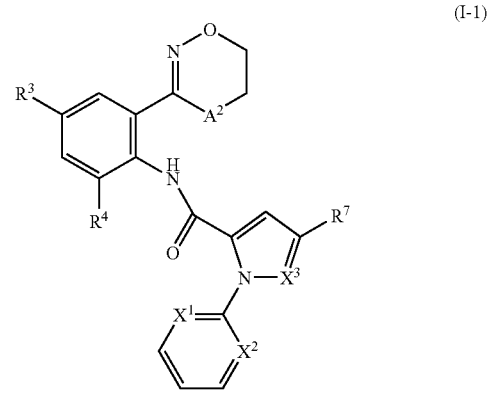

(I-1)

wherein:
$A^2$ is oxygen,
$R^3$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl,
$R^4$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, and
$X^1$ is N, CH, CF, CCl, CBr or CI,
$X^2$ is N or $CR^9$,
$X^3$ is N or CH,
$R^7$ is hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalklsulphonyl or ($C_1$-$C_4$-alkyl)$C_1$-$C_4$-alkoxyimino, and
$R^9$ is hydrogen, $C_3$-$C_6$-alkyl, $C_3$-$C_6$-cycloalkyl $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio,
or a N-oxide or salt thereof.

2. The compound of claim 1, wherein:
$R^3$ is hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio,
$R^4$ is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloakynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl,
or a N-oxide or salt thereof.

3. The compound of claim 1, wherein:
$A^1$ is oxygen,
$R^3$ is hydrogen, $C_1$-$C_4$-alkyl, $C_1$-$C_2$-haloalkyl, halogen, cyano or $C_1$-$C_2$-haloalkoxy,
$R^4$ is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, $X^1$ is CCl and $X^2$ is CH, or
$X^1$ is CF and $X^2$ is CCl, or
$X^1$ is CCl and $X^2$ is CCl, or
$X^1$ is N and $X^2$ is CF, or
$X^1$ is N and $X^2$ is CCl, or
$X^1$ is N and $X^2$ is CBr, or
$X^1$ and $X^2$ are N, and
$R^7$ is hydrogen, halogen or $C_1$-$C_4$-haloalkyl.

4. A compound of formula (II)

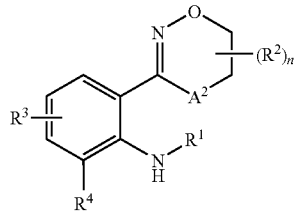

(II)

wherein:
A$^2$ is oxygen
$R^1$ is hydrogen, amino, hydroxyl or $C_1$-$C_6$-alkyl, $C_2$-$C_6$-alkenyl, $C_2$-$C_6$-alkynyl or $C_3$-$C_6$-cycloalkyl, each optionally mono- or polysubstituted by identical or different substituents, where the substituents independently of one another are selected from the group consisting of halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino and ($C_1$-$C_4$-alkyl)-$C_3$-$C_6$-cycloalkylamino, $R^2$ independently of one another is $C_1$-$C_6$-alkyl, $C_2$-$C_6$-alkenyl, $C_2$-$C_6$-alkynyl, $C_3$-$C_6$-cycloalkyl, each optionally mono- or polysubstituted by identical or different substituents, where the substituents independently, of one another are selected from the group consisting of halogen, cyano, nitro, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, ($C_1$-$C_6$-alkoxy)carbonyl, ($C_1$-$C_6$-alkyl)carbonyl and $C_3$-$C_6$-trialkylsilyl, n is 0 to 4, $R^3$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, SF$_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkcoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, and $R^4$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, or a N-oxide or salt thereof.

5. A pesticide composition comprising at least one compound of claim 1 and an auxiliary.

6. A method for treating animal pests, comprising contacting a compound of claim 1 with animal pests, their habitat, or both, wherein said animal pests are selected from the group consisting of insects, arachnids, helminths, nemaatodes, and molluscs, or a combination thereof.

7. A method of preparing a pesticide composition, said method comprising admixing a compound of claim 1 with extenders or surfactants, or both.

8. A method for treating seed, comprising contacting said seed with a compound of claim 1.

9. A method for treating transgenic plants, comprising contacting said transgenic plants with a compound of claim 1.

10. A method for treating seed of transgenic plants, comprising contacting said seed of transgenic plants with a compound of claim 1.

11. A seed which has been treated with a compound of claim 1.

12. A method of preparing a compound of formula (I),

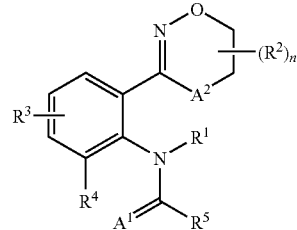

(I)

wherein:
A$^1$ is oxygen,
comprising reacting a compound of formula (II)

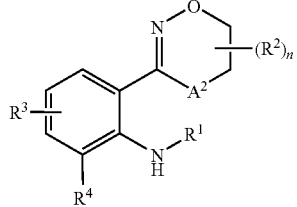

(II)

wherein:
A$^2$ is oxygen, $R^1$ is hydrogen, amino, hydroxyl or $C_1$-$C_6$-alkyl, $C_2$-$C_6$-alkenyl, $C_2$-$C_6$-alkynyl or $C_3$-$C_6$-cycloalkyl, each optionally mono- or polysubstituted by identical or different substituents, where the substituents independently of one another are selected from the group consisting of halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino and ($C_1$-$C_4$-alkyl)-$C_3$-$C_6$-cycloalkylamino, $R^2$ independently of one another is $C_1$-$C_6$-alkyl, $C_2$-$C_6$-alkenyl, $C_2$-$C_6$-alkynyl, $C_3$-$C_6$-cycloalkyl, each optionally mono- or polysubstituted by identical or different substituents, where the substituents independently of one another are selected from the group consisting of halogen, cyano, nitro, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, ($C_1$-$C_6$-alkoxy)carbonyl, ($C_1$-$C_6$-alkyl)carbonyl and $C_3$-$C_6$-trialkylsilyl, n is 0 to 4, $R^3$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, and $R^4$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, with an acid chloride of formula (III)

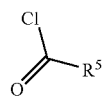
(III)

wherein:

$R^5$ is a 5- or 6-membered heteroaromatic ring optionally mono- or polysubstituted by identical or different substituents, where the substituents independently of one another are selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, $C_3$-$C_6$-trialkylsilyl, ($C_1$-$C_4$-alkyl)($C_1$-$C_4$-alkoxy)imino, or is selected from the group consisting of phenyl, benzoyl, phenoxy, 5- or 6-membered heteroaromatic rings and aromatic 8-, 9- or 10-membered fused heterobicyclic ring systems, where each of the aromatic, heteroaromatic or aromatic heterobicyclic systems is optionally mono- or polysubstituted by identical or different substituents, where the substituents independently of one another are selected from the group consisting of $C_1$-$C_6$-alkyl, $C_2$-$C_4$-alkenyl, $C_2$-$C_4$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, ($C_1$-$C_4$-alkyl)amino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_2$-$C_8$-alkyl)aminocarbonyl, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino and $C_3$-$C_6$-trialkylsilyl.

13. A method of preparing a compound of formula (I),

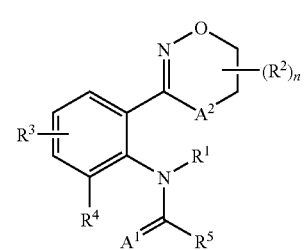
(I)

wherein:

$A^1$ is sulphur, comprising reacting a compound of formula (I-a)

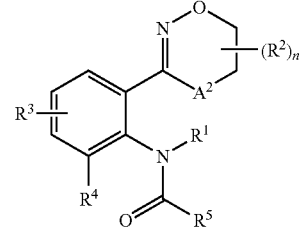
(I-a)

wherein:

$A^2$ is oxygen, $R^1$ is hydrogen, amino, hydroxyl or $C_1$-$C_6$-alkyl, $C_2$-$C_6$-alkenyl, $C_2$-$C_6$-alkynyl or $C_3$-$C_6$-cycloalkyl, each optionally mono- or polysubstituted by identical or different substituents, where the substituents independently of one another are selected from the group consisting of halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino and ($C_1$-$C_4$-alkyl)-$C_3$-$C_6$-cycloalkylamino, $R^2$ independently of one another is $C_1$-$C_6$-alkyl, $C_2$-$C_6$-alkenyl, $C_2$-$C_6$-alkynyl, $C_3$-$C_6$-cycloalkyl, each optionally mono- or polysubstituted by identical or different substituents, where the substituents independently of one another are selected from the group consisting of halogen, cyano, nitro, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, ($C_1$-$C_6$-alkoxy)carbonyl, ($C_1$-$C_6$-alkyl)carbonyl and $C_3$-$C_6$-trialkylsilyl, n is 0 to 4, $R^3$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, $R^4$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, and $R^5$ is a 5- or 6-membered heteroaromatic ring optionally mono- or polysubstituted by identical or different substituents, where the substituents independently of one another are selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, $C_3$-$C_6$-trialkylsilyl, ($C_1$-$C_4$-alkyl)($C_1$-$C_4$-alkoxy)imino, or is selected from the group consisting of phenyl, benzoyl, phenoxy, 5- or 6-membered heteroaromatic rings and aromatic 8-, 9- or 10-membered fused heterobicyclic ring systems, where each of the aromatic, heteroaromatic or aromatic heterobicyclic systems is optionally mono- or polysubstituted by identical or different substituents, where the substituents independently of one another are selected from the group consisting of $C_1$-$C_6$-alkyl, $C_2$-$C_4$-alkenyl, $C_2$-$C_4$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, ($C_1$-$C_4$-alkyl)amino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_2$-$C_8$-alkyl)aminocarbonyl, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino and $C_3$-$C_6$-trialkylsilyl, with a sulphurizing agent.

14. A method of preparing a compound of formula (II), wherein:
$R^1$ is not hydrogen,
comprising reacting a compound of formula (II)

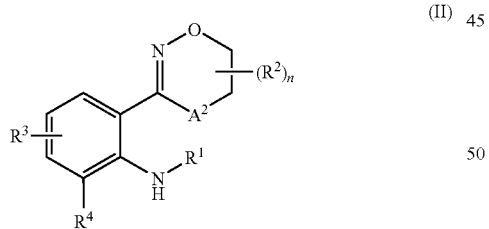

(II)

wherein:
$A^2$ is oxygen,
$R^1$ is hydrogen,
$R^2$ independently of one another is $C_1$-$C_6$-alkyl, $C_2$-$C_6$-alkenyl, $C_2$-$C_6$-alkynyl, $C_3$-$C_6$-cycloalkyl, each optionally mono- or polysubstituted by identical or different substituents, where the substituents independently of one another are selected from the group consisting of halogen, cyano, nitro, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, ($C_1$-$C_6$-alkoxy)carbonyl, ($C_1$-$C_6$-alkyl)carbonyl and $C_3$-$C_6$-trialkylsilyl,
n is 0 to 4, $R^3$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)amino, ($C_1$-$C_4$-haloalkyl)($C_1$-$C_4$-alkoxy)imino or $C_3$-$C_6$-trialkylsilyl, and $R^4$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, (A) with an alkylating agent in the presence of a base in the presence of a diluent, or (B) with an alkylating agent first in a condensation reaction in the presence of a diluent and second with a reducing agent in the presence of a diluent.

15. A method of preparing a compound of formula (II-a)

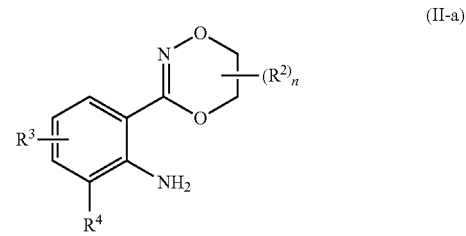

(II-a)

wherein:
$R^2$ independently of one another is $C_1$-$C_6$-alkyl, $C_2$-$C_6$-alkenyl, $C_2$-$C_6$-alkynyl, $C_3$-$C_6$-cycloalkyl, each optionally mono- or polysubstituted by identical or different substituents, where the substituents independently of one another are selected from the group consisting of halogen, cyano, nitro, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, ($C_1$-$C_6$-alkoxy)carbonyl, ($C_1$-$C_6$-alkyl)carbonyl and $C_3$-$C_6$-trialkylsilyl,
n is 0 to 4, $R^3$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$- haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_1$-haloalkyl)($C_1$-$C_4$-alkoxy)imino or $C_3$-$C_6$-trialkylsilyl, and $R^4$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, comprising reacting a compound having formula (IV):
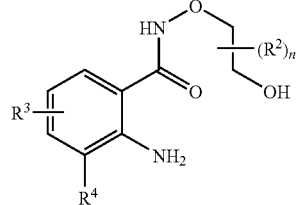
with an activating agent, optionally in the presence of a diluent.
16. The compound of claim 1, selected from the group consisting of:
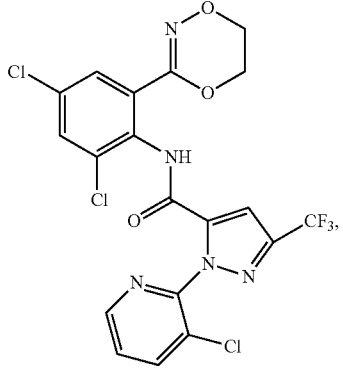
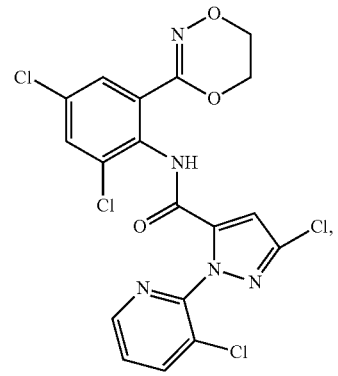
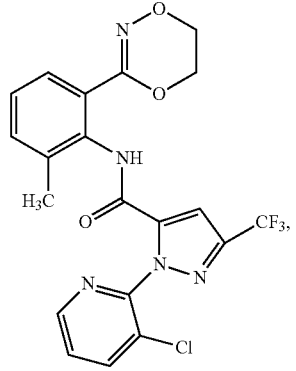
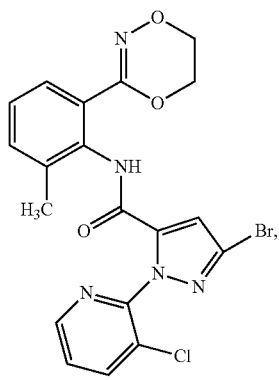
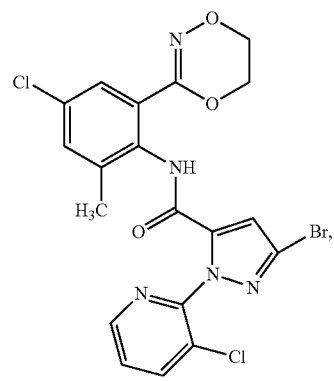
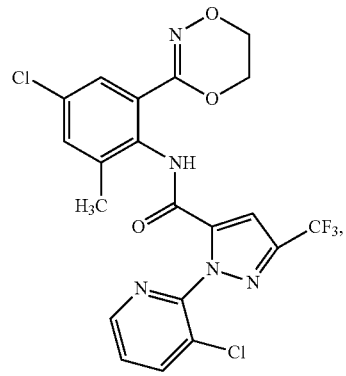
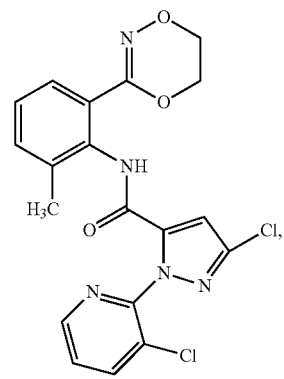

-continued
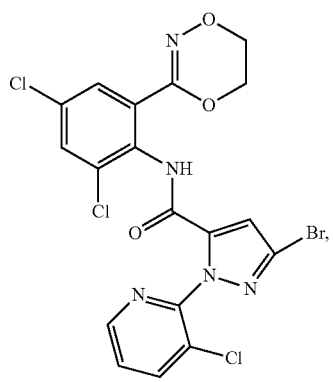
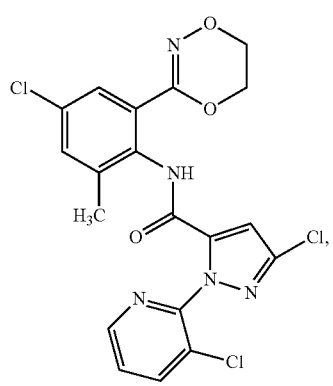
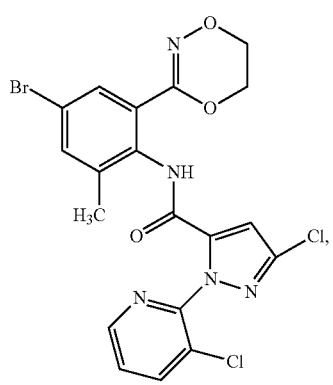
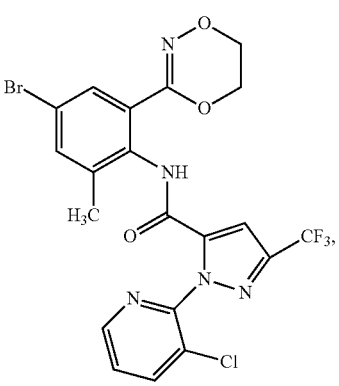
-continued
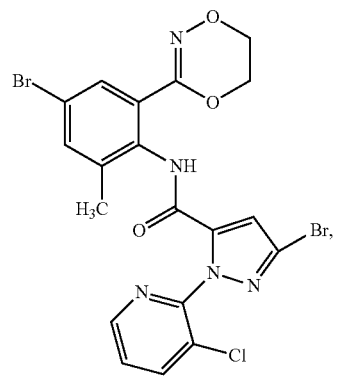
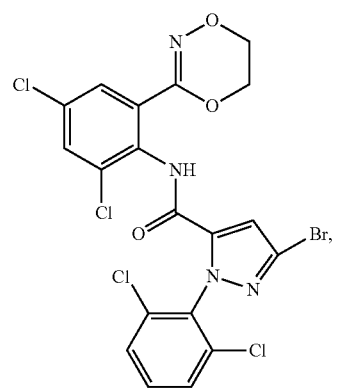
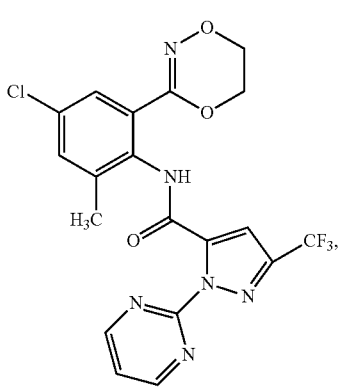
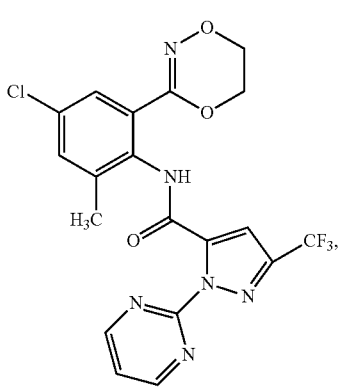

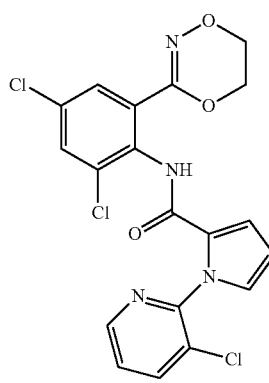
and
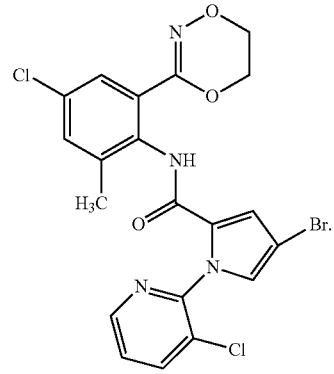
* * * * *